US012636169B2

(12) United States Patent
Neuvirth et al.

(10) Patent No.: US 12,636,169 B2
(45) Date of Patent: May 26, 2026

(54) PROSTHETIC FOOT

(71) Applicant: Starfish Holding, LLC, Rochester, MN (US)

(72) Inventors: Jill Neuvirth, Bloomfield Hills, MI (US); Brandon Sampson, Pine Island, MN (US)

(73) Assignee: Starfish Holding, LLC, Rochester, MN (US)

( * ) Notice: Subject to any disclaimer, the term of this patent is extended or adjusted under 35 U.S.C. 154(b) by 0 days.

(21) Appl. No.: 17/814,291

(22) Filed: Jul. 22, 2022

(65) Prior Publication Data

US 2023/0021935 A1      Jan. 26, 2023

Related U.S. Application Data

(60) Provisional application No. 63/203,431, filed on Jul. 22, 2021.

(51) Int. Cl.
*A61F 2/66*          (2006.01)
*A61F 2/50*          (2006.01)
*A61F 2/80*          (2006.01)

(52) U.S. Cl.
CPC .................. *A61F 2/66* (2013.01); *A61F 2/80* (2013.01); *A61F 2002/5083* (2013.01); *A61F 2002/6614* (2013.01); *A61F 2002/6657* (2013.01)

(58) Field of Classification Search
CPC ...... A61F 2002/6657; A61F 2002/6671; A61F 2002/6678
See application file for complete search history.

(56) References Cited

U.S. PATENT DOCUMENTS

| | | | | |
|---|---|---|---|---|
| 5,181,932 A | * | 1/1993 | Phillips ..................... | A61F 2/66 623/55 |
| 5,442,528 A | * | 8/1995 | Vandenbelt ............ | B42D 3/123 362/198 |
| 5,653,767 A | * | 8/1997 | Allen ........................ | A61F 2/68 623/55 |
| 5,695,527 A | * | 12/1997 | Allen ........................ | A61F 2/68 623/55 |
| 2005/0171618 A1 | * | 8/2005 | Christensen .............. | A61F 2/66 623/56 |
| 2011/0107581 A1 | * | 5/2011 | Williams .................. | A61F 2/66 264/239 |
| 2012/0271434 A1 | * | 10/2012 | Friesen ..................... | A61F 2/66 623/55 |
| 2016/0008147 A1 | * | 1/2016 | Marlin ...................... | A61F 2/66 623/55 |
| 2019/0125552 A1 | * | 5/2019 | Day ...................... | A61F 2/6607 |

* cited by examiner

*Primary Examiner* — Jerrah Edwards
*Assistant Examiner* — Maximilian Tobias Spencer
(74) *Attorney, Agent, or Firm* — Fredrikson & Byron, P.A.

(57)          ABSTRACT
A prosthetic foot includes a cap, a retaining element and a plurality of blades. Each of the plurality of blades includes a proximal portion coupled with the cap, a middle portion coupled with the retaining element and a distal portion extending outwardly from the retaining element.

11 Claims, 7 Drawing Sheets

PROSTHETIC FOOT

BACKGROUND

Current prosthetic limbs are designed for a variety of different applications. For example, a prosthetic limb may take the shape of a foot or take the shape of a different structure depending on a particular use of the prosthetic limb.

SUMMARY

A prosthetic foot includes a cap, a retaining element and a plurality of blades. Each of the plurality of blades includes a proximal portion coupled with the cap, a middle portion coupled with the retaining element and a distal portion extending outwardly from the retaining element.

DETAILED DESCRIPTION

Figure 1:
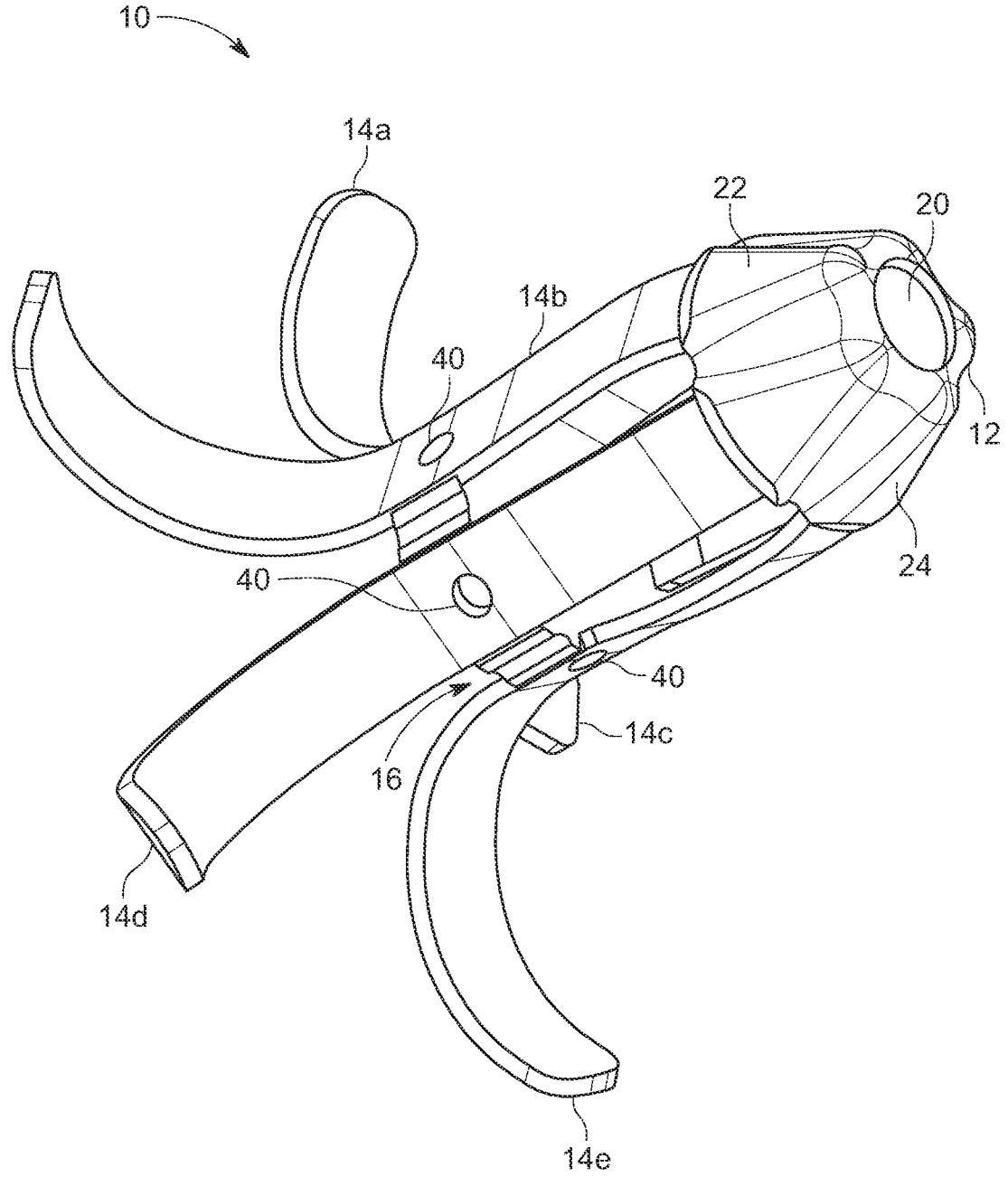
FIG. 1 is a perspective views of a prosthetic foot.
Figure 2:
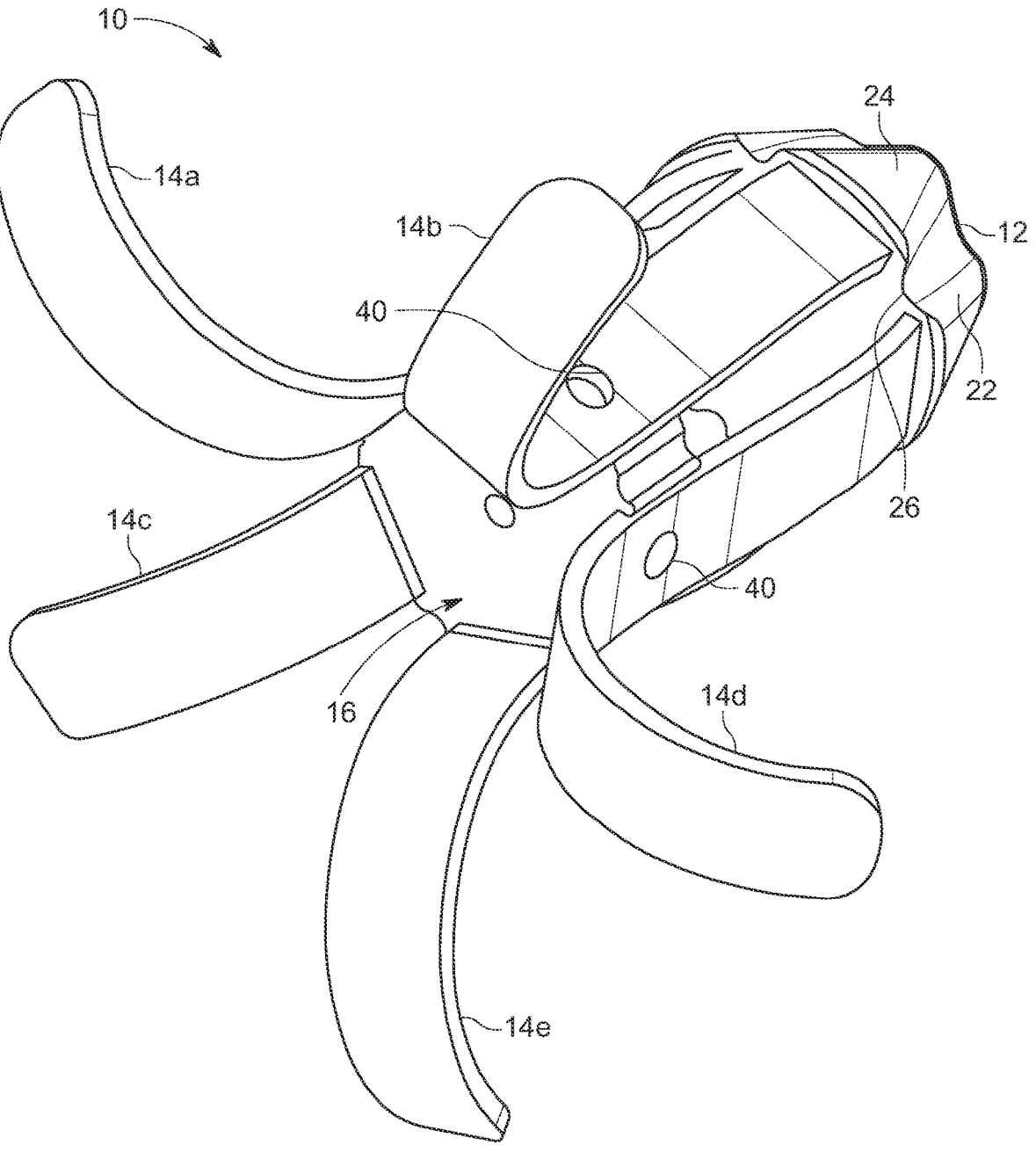
FIG. 2 is another perspective view of the prosthetic foot of FIG. 1.
Figure 3:
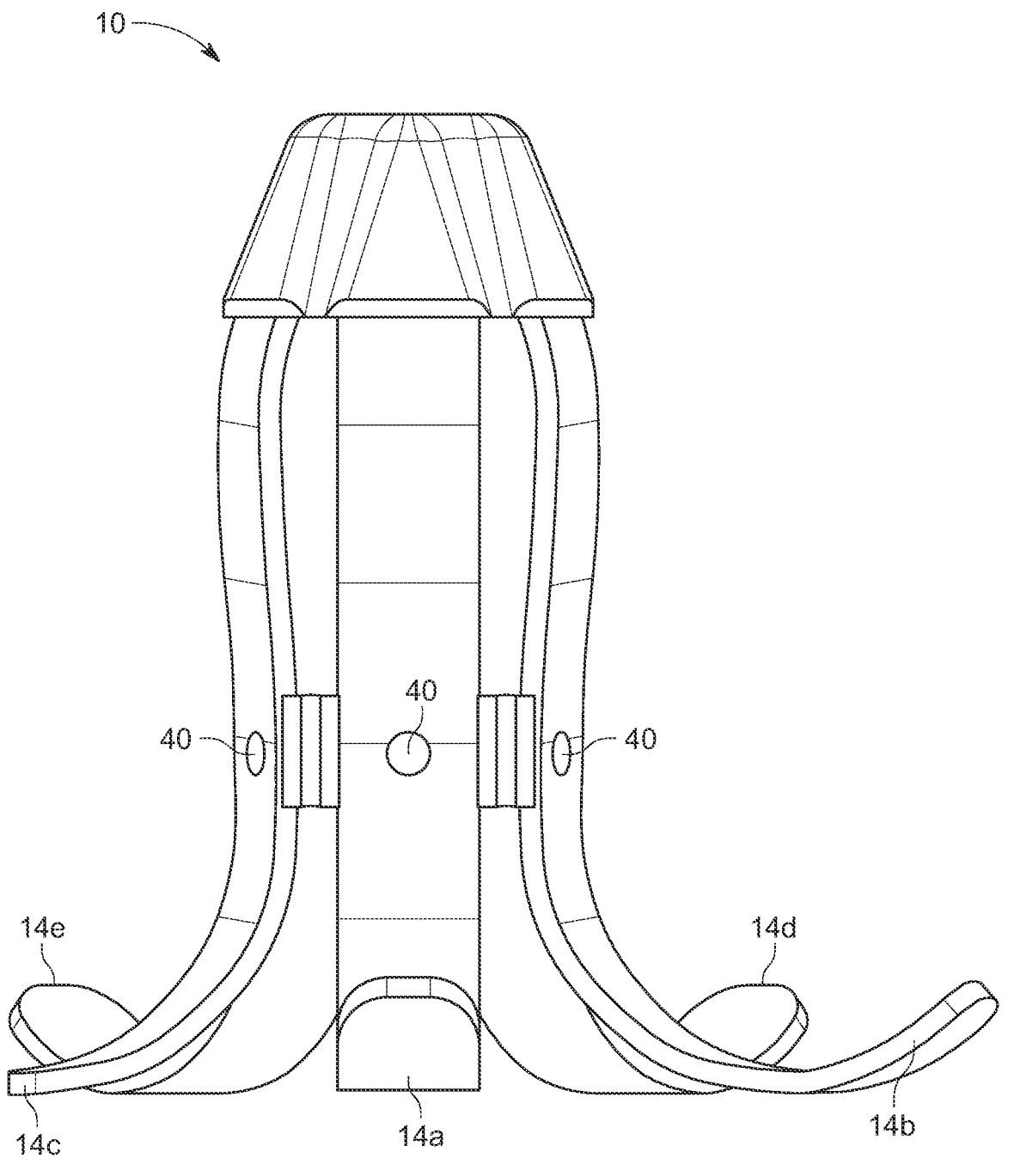
FIG. 3 is a front elevation view of the prosthetic foot of FIG. 1.
Figure 4:
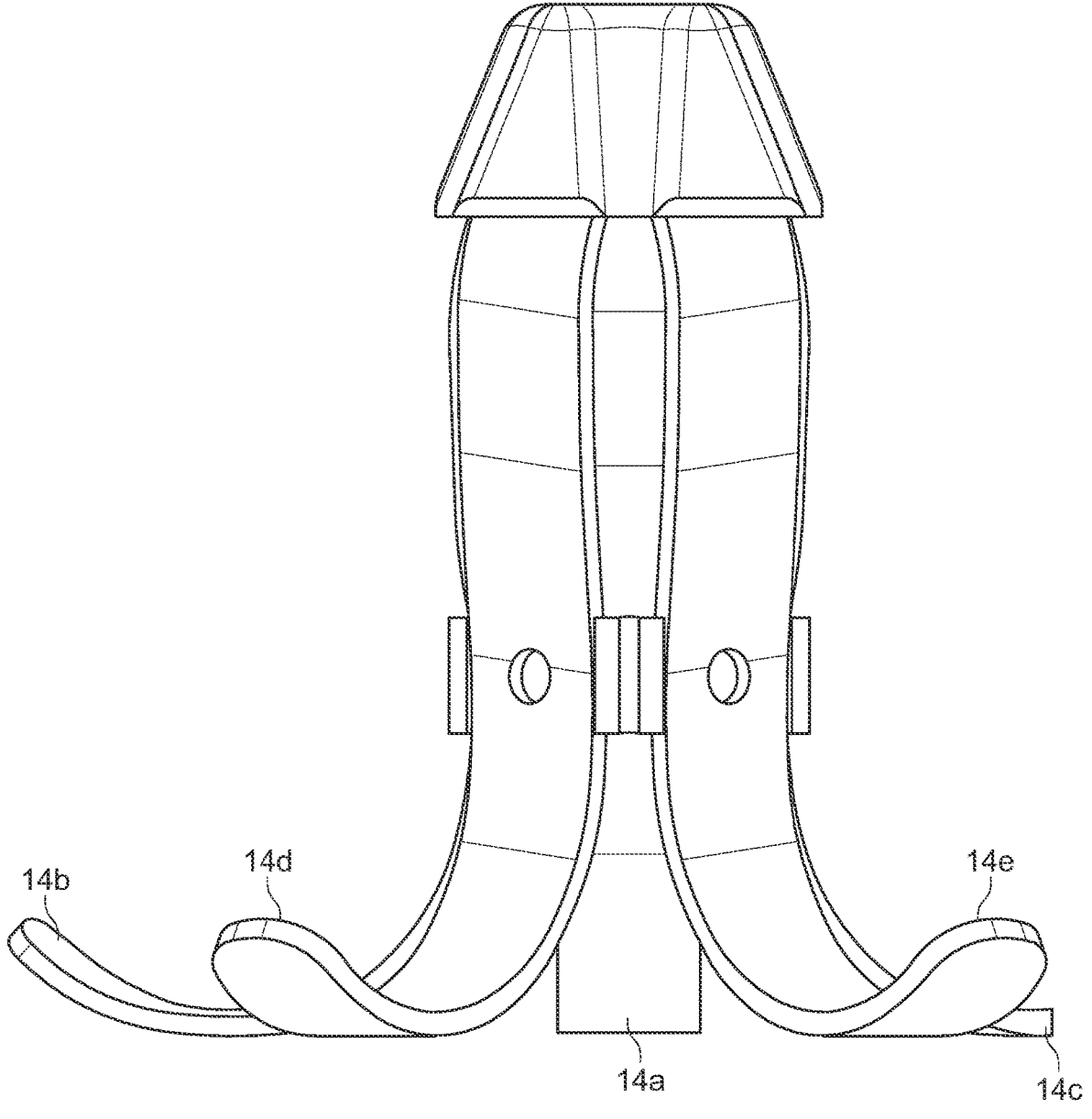
FIG. 4 is a rear elevation view of the prosthetic foot of FIG. 1.
Figure 5:
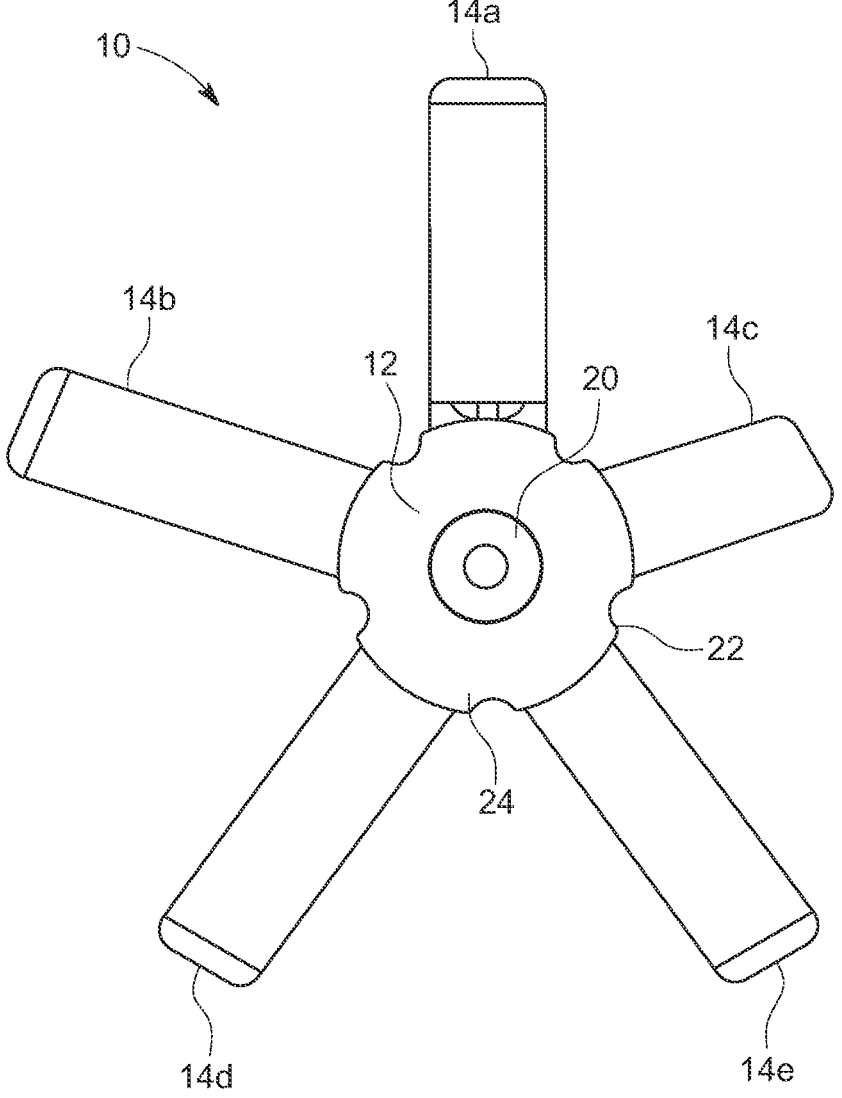
FIG. 5 is a top plan view of the prosthetic foot of FIG. 1.
Figure 6:
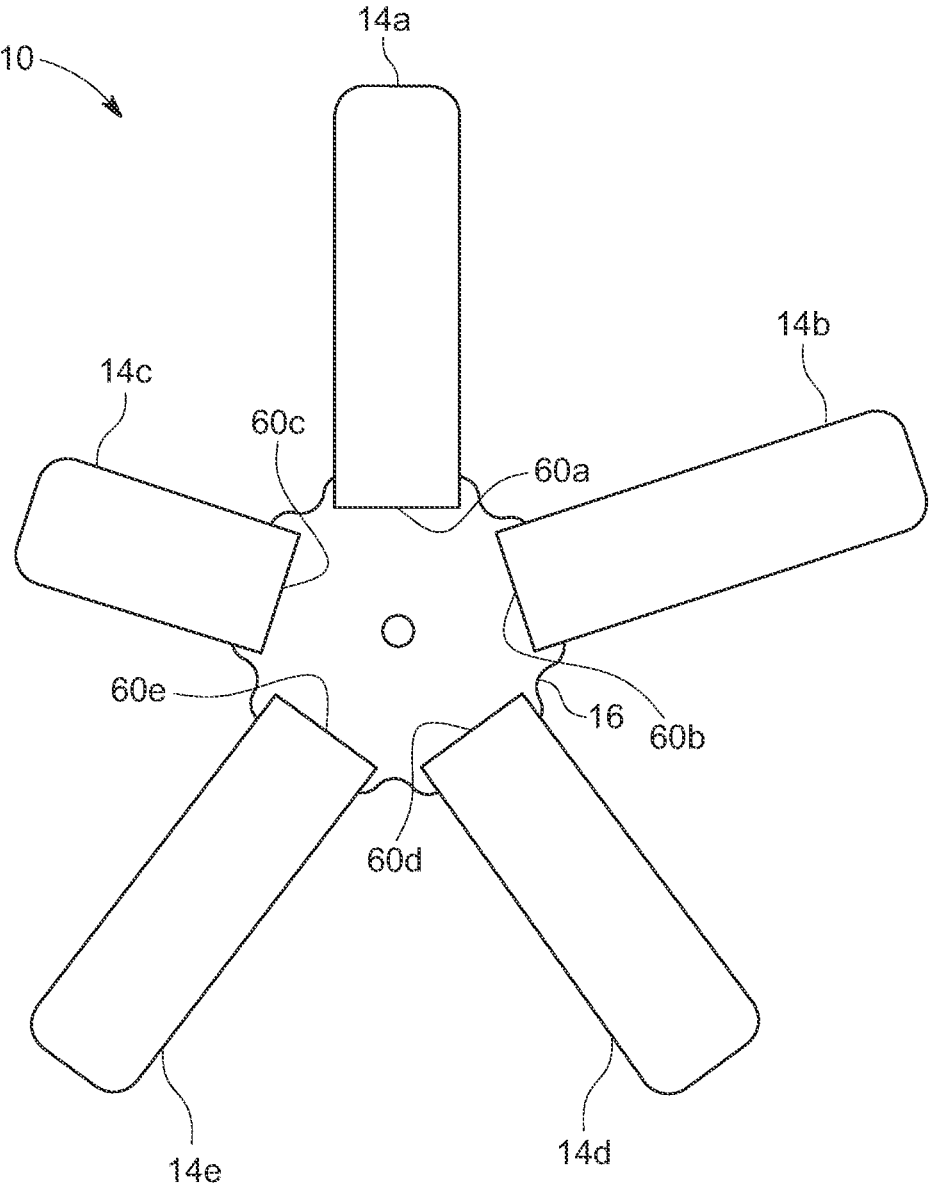
FIG. 6 is a bottom view of the prosthetic foot of FIG. 1.

FIGS. 1-7 illustrate various views of an exemplary prosthetic foot 10 that includes a proximal connecting element 12, a plurality of blades 14 extending from the connecting element 12 and a retaining element 16 coupled with the plurality of blades 14. In general, the connecting element 12 is configured to be coupled to a limb of a user (e.g., a pylon), with the plurality of blades extending downwardly to the retaining element 16 and outwardly in a radial arrangement so as to support a user.

In the embodiment illustrated, the connecting element 12 is formed of a truncated pentagonal pyramid defining an upper aperture or socket 20 configured to receive a pylon connected with a limb of a user and a wall 22 extending about a periphery of the socket 20. Other shapes besides a truncated pentagonal pyramid can be utilized as desired, such as a truncated cone, an irregular pyramid, a hemisphere and others. Regardless of the selected shape, the wall 22 defines an exterior surface 24 and an interior surface 26. The plurality of blades 14 are positioned adjacent to and coupled with the interior surface 26 and extend distally from the connecting element 12. In the illustrated embodiment, a number of the plurality of blades selected is five (denoted as blades 14a-14e), although other numbers of blades can be selected as desired (e.g., two, three, four, more than five). Each of the blades 14 can be formed of various materials such as carbon fiber, fiber glass, metal, etc. The material selected for the blades can include a desired flexibility depending upon a particular use for the prosthetic foot 10, one or more characteristics of the user and/or other factors and/or combinations of factors.

Figure 7:
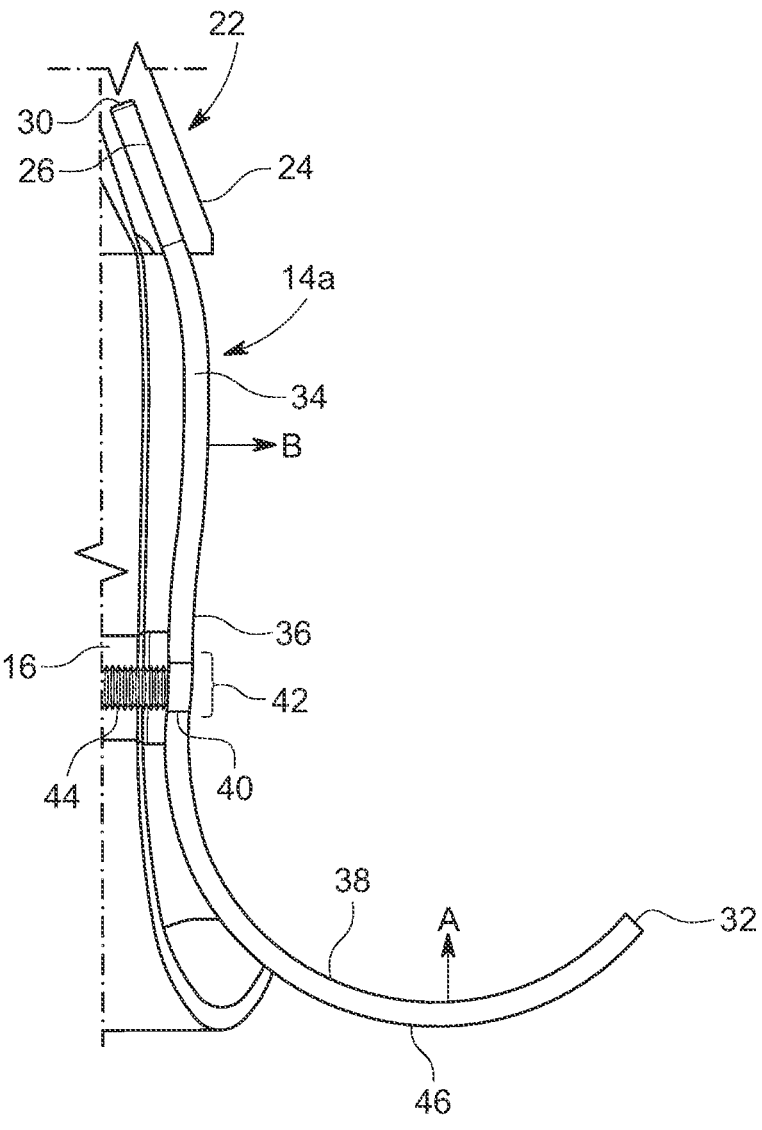
FIG. 7 is a sectional side view of the prosthetic foot of FIG. 1.

With reference to FIG. 7, each blade 14 extends from a proximal end 30 to a distal end 32 and defines a proximal portion 34, a middle portion 36 and a distal portion 38. The proximal portion 34, in the illustrated embodiment, is attached to the interior surface 26 (e.g., with an adhesive) and defines an outward bend between the connecting element 12 and the retaining element 16. In other embodiments, the proximal portion 34 can have a bend of a greater extent or a lesser extent. In another embodiment, the proximal portion 34 can be straight. In one embodiment, the proximal portion can be pre-loaded to desired characteristics.

The middle portion 36 includes an aperture 40 to receive a corresponding fastener 42. In one embodiment, the fastener 42 can be secured to the retaining element 16 using a threaded aperture 44 positioned in the retaining element 16. In alternative embodiments, aperture 40 can form an elongated slot that allows positioning of the retaining element 16 with respect to a contact surface 46 of the blade 14. In yet another embodiment, a plurality of apertures can be positioned along the blade 14 so as to locate the retaining element 16 at different heights with respect to the contact surface 46. The distal portion 38 includes a selected radius of curvature extending from the fastener 42 to the distal end 32 of the blade 14. The radius of curvature can be selected as desired to provide desired characteristics.

The retaining element 16 provides a support structure to connect each of the plurality of blades 14 to one another. To that end, in addition to providing a threaded aperture 44 for each of the blades, retaining element 16 can also define a corresponding slot 60 (i.e., slots 60a-60e) to locate each of the plurality of blades 14 about a periphery of the prosthetic foot 10. During assembly of prosthetic foot 10, the plurality of blades 14 can be positioned within a corresponding slot 60 and a fastener 42 is positioned within a corresponding aperture 40 and used to secure each of the plurality of blades 14 to the retaining element 16. The retaining element 16 can be formed of various different materials and in one embodiment is formed of a compliant shock absorbing material. In the illustrated embodiment, the retaining element 16 is positioned inboard (i.e., a mounting surface of the retaining element 16 faces an inner side of each blade 14) of the plurality of blades 14. In other embodiments, the retaining element 16 can be positioned outboard of the plurality of blades 14 (i.e., a mounting surface of the retaining element 16 faces an outer side of each blade 14). Cap 12 is positioned over corresponding proximal ends 30 of the plurality of blades 14 and cap 12 can be secured to the proximal ends 30.

A pylon connected to a limb of a user is inserted into the socket 20 to secure the prosthetic foot 10 to the pylon. The prosthetic foot 10 can be oriented with respect to the user such that blade 14a can be pointed forward (i.e., directed in a similar orientation to toes of a foot and simulating a forefoot), blades 14d and 14e can be pointed rearward (i.e., directed in a similar orientation to a heel of a foot and simulating a hindfoot) and blades 14b and 14c can be pointed sideways (i.e., simulating a midfoot). Together, each of the plurality of blades 14 provides a stable support for a user that can be utilized for a variety of different activities. Each of the blades 14a-e can have a different length as desired. For example, blade 14c is illustrated as having a shorter length than blades the remaining blades 14a, 14b, 14d or 14e.

During use (e.g., standing, walking), the blades 14 are configured to deflect to provide stability. For example, as shown in FIG. 7, the distal portion 38 of the blade 14 will deflect upward (as indicated by arrow A) and pivot about fastener 42. Additionally, the proximal portion 34 of the blade 14 will deflect outward (as indicated by arrow B) between proximal end 30 and fastener 42. The amount of deflection represented by arrows A and B can be adjusted based on a number of different factors, such as stiffness of the blade, height of the fastener 42 with respect to contact surface 46, distance between cap 22 and fastener 42, distance of contact surface 46 with respect to a central vertical axis of the prosthetic foot 10, radius of curvature of proximal portion 34 and/or distal portion 38, and others. The prosthetic foot 10 can be useful for various activities such as training, yoga and others.

Various embodiments of the invention have been described above for purposes of illustrating the details thereof and to enable one of ordinary skill in the art to make and use the invention. The details and features of the disclosed embodiment[s] are not intended to be limiting, as many variations and modifications will be readily apparent to those of skill in the art. Accordingly, the scope of the present disclosure is intended to be interpreted broadly and to include all variations and modifications coming within the scope and spirit of the appended claims and their legal equivalents.

The invention claimed is:

1. A prosthetic foot comprising:
   a cap defining an interior surface and an exterior surface;
   a retaining element; and
   a plurality of blades, each blade including a proximal portion terminating at a proximal end, a middle portion coupled with the retaining element and a distal portion extending outwardly from the retaining element, wherein the cap is positioned over the proximal end of each of the plurality of blades and the proximal portion of each of the plurality of blades is coupled to the interior surface of the cap,
   wherein the proximal portion and the distal portion of each blade are on a same side of the retaining element and the cap, and the plurality of blades are on different sides of the retaining element and the cap, the plurality of blades comprises an anterior oriented blade, a posterior oriented blade, and a lateral and/or medial oriented blade; and
   wherein the retaining element comprises a plurality of apertures, each of the plurality of blades comprises an opening, and the middle portion of the plurality of blades is coupled with the retaining element via a fastener inserted through the opening and into one of the plurality of apertures of the retaining element.

2. The prosthetic foot of claim 1, wherein a number of the plurality of blades is five.

3. The prosthetic foot of claim 1, wherein the blades are formed of at least one of fiberglass and carbon fiber.

4. The prosthetic foot of claim 1, wherein the plurality of blades includes a first blade simulating a forefoot, second and third blades simulating a midfoot and fourth and fifth blades simulating a hindfoot.

5. The prosthetic foot of claim 1, wherein the cap defines a socket configured to receive a pylon of a prosthetic limb.

6. The prosthetic foot of claim 1, wherein each of the plurality of blades defines an inner surface and an outer surface, and the retaining element is positioned between the inner surface of each of the plurality of blades.

7. The prosthetic foot of claim 1, wherein one of the plurality of blades is shorter than one other of the plurality of blades.

8. The prosthetic foot of claim 1, wherein:
   the cap defines an upper socket configured to receive a pylon connected to a limb of a user and a wall extending about a periphery of the socket;
   the wall defines the interior surface and the exterior surface; and
   the plurality of blades are coupled to the interior surface of the wall.

9. The prosthetic foot of claim 1, wherein the retaining element comprises a plurality of slots, and each of the plurality of blades is positioned in a corresponding one of the plurality of slots.

10. The prosthetic foot of claim 1, wherein:
    each the plurality of blades defines a contact surface between the distal portion and the middle portion coupled with the retaining element;
    the prosthetic foot defines a longitudinal axis extending from the cap to the contact surface; and
    each blade of the plurality of blades curves outwardly from the longitudinal axis over a region from the middle portion coupled with the retaining element to the distal portion.

11. The prosthetic foot of claim 1, wherein the plurality of apertures are threaded and the fastener is threadingly inserted through the opening and into one of the plurality of apertures of the retaining element.

* * * * *